US011015119B2

(12) United States Patent
Egoshi

(10) Patent No.: US 11,015,119 B2
(45) Date of Patent: May 25, 2021

(54) ULTRAVIOLET LIGHT-EMITTING PHOSPHOR, LIGHT-EMITTING ELEMENT, AND LIGHT-EMITTING DEVICE

(71) Applicant: DYDEN CORPORATION, Fukuoka (JP)

(72) Inventor: Kiichiro Egoshi, Miyaki-gun Saga (JP)

(73) Assignee: Dyden Corporation, Fukuoka (JP)

( * ) Notice: Subject to any disclaimer, the term of this patent is extended or adjusted under 35 U.S.C. 154(b) by 330 days.

(21) Appl. No.: 15/778,918

(22) PCT Filed: Nov. 18, 2016

(86) PCT No.: PCT/JP2016/084279
§ 371 (c)(1),
(2) Date: May 24, 2018

(87) PCT Pub. No.: WO2017/094532
PCT Pub. Date: Jun. 8, 2017

(65) Prior Publication Data

US 2018/0355246 A1 Dec. 13, 2018

(30) Foreign Application Priority Data

Nov. 30, 2015 (JP) ............................ JP2015-233671

(51) Int. Cl.

| | |
|---|---|
| ***C09K 11/77*** | (2006.01) |
| ***H01L 33/50*** | (2010.01) |
| ***H05B 33/14*** | (2006.01) |
| ***H01L 33/00*** | (2010.01) |
| ***A61L 2/00*** | (2006.01) |
| ***A61L 2/10*** | (2006.01) |
| ***A61N 5/06*** | (2006.01) |

(52) U.S. Cl.
CPC ........ *C09K 11/7774* (2013.01); *A61L 2/0052* (2013.01); *A61L 2/10* (2013.01); *A61N 5/06* (2013.01); *H01L 33/00* (2013.01); *A61L 2202/11* (2013.01); *A61N 2005/0656* (2013.01); *A61N 2005/0661* (2013.01)

(58) Field of Classification Search
CPC ..... C09K 11/7774; C09K 11/06; C09K 11/64; C09K 11/642; C09K 11/7706; C09K 2211/1416; H01L 33/50; H01L 33/502; A61L 2/0052; A61L 2/10; A61L 2202/11; A61N 2005/0656; A61N 2005/0661; A61N 5/06; H05B 33/14
See application file for complete search history.

(56) References Cited

U.S. PATENT DOCUMENTS

2015/0287587 A1* 10/2015 Honda .................. B05D 5/061
250/458.1
2015/0329777 A1* 11/2015 Hoppe ................. C04B 35/117
428/220

FOREIGN PATENT DOCUMENTS

EP 2 913 376 A1 9/2013
EP 2 913 378 A1 9/2013

OTHER PUBLICATIONS

Zorenko et al., "Luminescence of La3+ and Sc3+ impurity centers in YAlO3 single-crystalline films", 2008, Journal of Luminescence, 128, pp. 595-602. (Year: 2008).*
EPO Examination Report, 6 Pages, dated May 28, 2020, Application No. 16 870 470.8-1105, Dyden Corporation.
Extended European Search Report, Application No./Patent No. 16870470.8-1105 / 3385356 PCT/JP2016084279, 8 pages, dated Apr. 16, 2019, The Hague.
Korea Office Action No. KR 10-2018-7009612, 5 Pages, dated Jul. 17, 2019.
Office Action in China No. CN 201680061089.X, 7 pages, no translation, dated Apr. 21, 2020.
Pergamon; Ultraviolet and Visable Luminescence Properties; 3 pages; www.elsevier.com/locate/radmeas. 2002.
Elsevier; ScienceDirect; Luminescence of La; Zorenko; Published 2007.
Elsevier; ScienceDirect; Novel UV-emitting single crystalline film; Zorenko; Published 2009.
JP 2015-233671 Decision to Grant and translation, dated Apr. 2017.
JP 2015-233671 Office Action and translation, dated Jan. 2017.

* cited by examiner

*Primary Examiner* — Matthew E. Hoban
*Assistant Examiner* — Lynne Edmondson
(74) *Attorney, Agent, or Firm* — Fay Sharpe LLP

(57) ABSTRACT

An ultraviolet light-emitting phosphor having excellent degradation resistance and emission intensity is provided. The ultraviolet light-emitting phosphor is a phosphor comprising yttrium element, scandium element, aluminum element and oxygen element, which is excited by irradiation of vacuum ultraviolet rays or electron beams to emit ultraviolet rays.

6 Claims, 6 Drawing Sheets

ULTRAVIOLET LIGHT-EMITTING PHOSPHOR, LIGHT-EMITTING ELEMENT, AND LIGHT-EMITTING DEVICE

TECHNICAL FIELD

The present invention relates to an ultraviolet light-emitting phosphor, which emits ultraviolet rays, and particularly to an ultraviolet light-emitting phosphor having excellent degradation resistance and emission intensity.

BACKGROUND ART

At present, the use of ultraviolet rays has been expanded to various fields such as medical care and photocatalysts, and the field of ultraviolet light emission is increasing in industrial value. Ultraviolet rays have a strong interaction with DNA, are effective in rendering the influenza virus, the norovirus or eumycetes such as candida harmless and its disinfection, and is not only effective in the disinfection of water, animals and plants and the disinfection of air and instruments at hospitals and homes as clean disinfection without the impartment of resistance to genes, but also expected to be practically used in a wide range of fields such as application to the decomposition of hardly decomposed substances, the synthesis of chemical substances, and the like, and medical application. The development and improvement of light-emitters that can present ultraviolet light emission have been advanced as a background to such a great industrial demand.

Mercury lamps, which mainly contain mercury, are used as light-emitters that present ultraviolet light emission for the present. This reason is because the mercury lamps can be manufactured at low cost and because emitted light with high energy is obtained simply.

However, problems such as a mercury lamp being incapable of controlling the emission wavelength variably and having a short life have been pointed out.

Additionally, it is regarded as questionable now mercury applying a large load to the natural environment. In view of environmental protection, the enforcement of the legal restrictions forbidding mercury production is also planned in the future. Due to such a background, the development of ultraviolet light-emitting light sources not containing mercury (mercury-free) is required immediately.

As a conventional light source that does not contain mercury and presents ultraviolet light emission, for example, a light source in which a $ZnAl_2O_4$ phosphor is irradiated with electron beams as an excitation source to emit ultraviolet rays is known (refer to Non Patent Literature 1).

CITATION LIST

Non Patent Literature

Non Patent Literature 1

Iguchi et al., Shingaku Giho (Communication Study Technique Report), pp. 5-8, The Institute of Electronics, Information and Communication Engineers (corporation), January, 2011

SUMMARY OF INVENTION

Technical Problem

However, firing in a reducing atmosphere is required for a conventional phosphor that emits ultraviolet rays (for example, $ZnAl_2O_4$). Therefore, there is a problem that in-process, degradation is marked in a ramp step (firing at 500 to 700° C. in the air atmosphere) in a manufacturing process. The situation is that the amount of ultraviolet rays emitted from the conventional ultraviolet light-emitting phosphor becomes insufficient due in part to the influence of the degradation and the emission intensity cannot reach an emission intensity required for practical use.

The present invention has been completed to solve the above-mentioned problem, and can suppress degradation in a manufacture process. The object thereof is to provide an ultraviolet light-emitting phosphor which has excellent degradation resistance and emission intensity.

Solution to Problem

The present inventors have earnestly repeated research and consequently found a new type of ultraviolet light-emitting phosphor that emits a high emission intensity of ultraviolet rays. Additionally, the present inventors have also found an excellent characteristic of the ultraviolet light-emitting phosphor having an excellent characteristic of the in-process degradation being very little and derived the present invention.

Specifically, an ultraviolet light-emitting phosphor disclosed and provided in the present application is an ultraviolet light-emitting phosphor, comprising yttrium element, scandium element, aluminum element and oxygen element, wherein the ultraviolet light-emitting phosphor is excited by the irradiation of vacuum ultraviolet rays or electron beams to emit ultraviolet rays. A light-emitting element that is characterized by comprising the ultraviolet light-emitting phosphor disclosed in the present application is also provided. A light-emitting device, comprising the light-emitting element disclosed in the present application is also provided.

DESCRIPTION OF EMBODIMENTS

Figure 1:
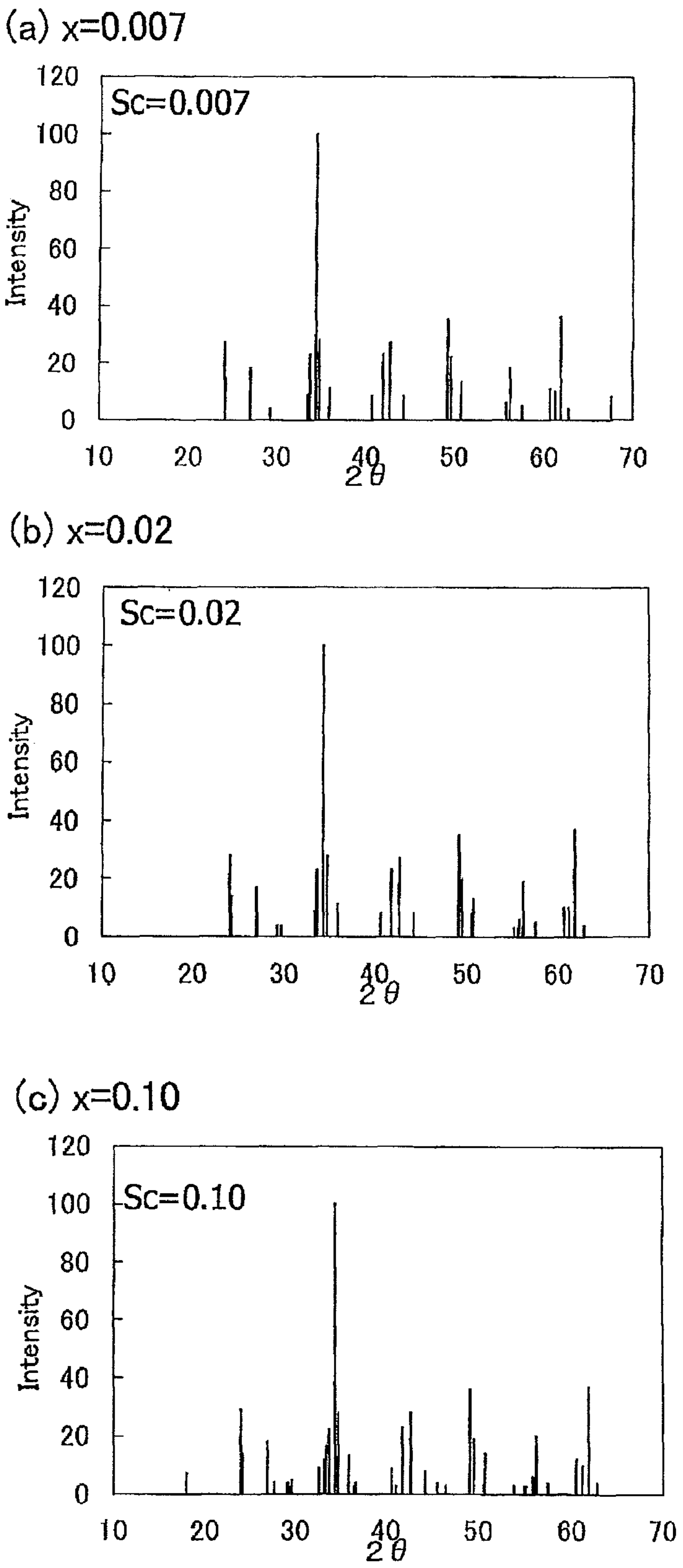
FIG. 1 shows the X-ray diffraction results of ultraviolet light-emitting phosphors according to Example 1 of the present invention.

As long as the ultraviolet light-emitting phosphor disclosed in the present application is a phosphor comprising yttrium element, scandium element, aluminum element and oxygen element, wherein the ultraviolet light-emitting phosphor is excited by the irradiation of vacuum ultraviolet rays or electron beams to emit ultraviolet rays, it is not particularly limited.

Although the excitation source is not particularly limited, vacuum ultraviolet rays or electron beams can be used. Vacuum ultraviolet rays means ultraviolet rays with a wavelength of 200 nm or less, and, for example, ultraviolet rays with a wavelength of 147 nm, ultraviolet rays with a wavelength of 172 nm or the like can be used.

The ultraviolet light-emitting phosphor disclosed in the present application can emit ultraviolet rays in various wavelength regions by the irradiation of such vacuum ultraviolet rays or electron beams. Since firing in a reducing atmosphere is not required, by far higher durability is obtained than that of the conventional ultraviolet light-emitting phosphors.

The ultraviolet light-emitting phosphor disclosed in the present application is not particularly limited, and can be represented as a general formula $(Y_{1-x}Sc_x)AlO_3$ (wherein $0<x<1$) as an example as long as the ultraviolet light-emitting phosphor is a phosphor comprising yttrium element (Y), aluminum element (Al) and scandium element (Sc).

Strong emission intensity is easily obtained from this ultraviolet light-emitting phosphor $(Y_{1-x}Sc_x)AlO_3$ when the fractional content of scandium element (Sc) is smaller, and meanwhile it tends to become difficult that sufficient emitted light is obtained when the fractional content of scandium element (Sc) is too small. From such a viewpoint, it is more preferable that $0.007 \leq x \leq 0.50$. From a viewpoint that emitted light having the wavelength of a still stronger peak is easily obtained, it is more preferable that $0.007 \leq x \leq 0.40$.

The present inventors have actually confirmed that the integrated emission intensity (a.u.) as to ultraviolet light emission is improved dramatically when the fractional content of yttrium element (Y) (1-x) exceeds 0.60 (namely, when x is smaller than 0.40) (refer to the below-mentioned Examples). Additionally, the present inventors have also confirmed that the peak wavelength of the ultraviolet light-emitting phosphor according to the present application is shortened gradually from around 300 nm when the fractional content of yttrium element (Y) (1-x) exceeds 0.60. More specifically, it is more preferable that $0.007 \leq x \leq 0.40$. In the case, this ultraviolet light-emitting phosphor $(Y_{1-x}Sc_x)AlO_3$ can exhibit the excellent characteristics of ultraviolet light with a shorter wavelength being obtained than around 300 nm and its integrated emission intensity being also improved dramatically.

The use of the ultraviolet light-emitting phosphor according to the present application is not particularly limited as long as its use is a use in which emitted ultraviolet light is used, but the ultraviolet light-emitting phosphor can be used as, for example, the use of disinfection (bactericidal lamp or the like) in terms of ultraviolet light with such a short wavelength being obtained with a high emission intensity. From this, the ultraviolet light-emitting phosphor according to the present application can function as a light source that can replace mercury lamps mainly used until now as a disinfection use.

For example, when this ultraviolet light-emitting phosphor $(Y_{1-x}Sc_x)AlO_3$ is used, specializing in the above-mentioned disinfection use, it is preferable that $0.007 \leq x \leq 0.4$ in terms of a suitable peak wavelength for the disinfection use being obtained at a short wavelength of around 300 nm or less. Additionally, it is more preferable that $0.007 \leq x \leq 0.25$ in terms of a more suitable peak wavelength for the disinfection use being obtained at a short wavelength of around 290 nm or less. For example, in a use in which a strong disinfection capability is required, it is still more preferable that $0.007 \leq x \leq 0.10$ in terms of a peak wavelength being obtained at a short wavelength of around 260 nm to around 270 nm or less. That is, the ultraviolet light-emitting phosphor according to the present application has the excellent characteristic of being capable of emitting ultraviolet light that is suitable for a disinfection use and exhibits an emission peak at around 300 nm or less (especially 260 nm to 270 nm).

Thus, the ultraviolet light-emitting phosphor disclosed in the present application enables obtaining not only the excellent effect of high emission intensity being obtained by irradiating vacuum ultraviolet rays but also additionally by far higher durability than that of the conventional ultraviolet light-emitting phosphors due to firing in a reducing atmosphere not being required. The excellent characteristic of being hardly subject to in-process degradation has been also confirmed actually (refer to the below-mentioned Examples).

The mechanism in which the ultraviolet light-emitting phosphor according to the present application exhibits the above-mentioned excellent effect is not clarified in detail yet. However, presumably there has happened such an organization that scandium element is preferably adapted to the physical configuration of atoms making up elements of yttrium, aluminum and oxygen constituting the phosphor to form an emission center capable of significantly promoting light emission and a structural factor allowing strong ultraviolet light emission has thus been incorporated. In other words, it is presumed that the phosphor is transferred more easily to an energy level allowing light emission in the specific ultraviolet band at the atomic level by irradiating vacuum ultraviolet rays or electron beams.

It is considered that scandium element maintains a state difficult to change in valence at the atomic level due to the physical configuration of atoms making up the elements of yttrium, aluminum and oxygen constituting the phosphor. It is therefore presumed that the phosphor forms a state difficult to deteriorate by external heat and chemical change.

In a method for obtaining the ultraviolet light-emitting phosphor according to the present application, respective compounds (for example, oxides) containing constituent elements are used as raw materials and mixed at a stoichiometric proportion that forms the composition of a desired phosphor. For example, as these materials, powders of aluminum oxide ($Al_2O_3$), yttrium oxide ($Y_2O_3$), and scandium oxide ($Sc_2O_3$) can be used.

The ultraviolet light-emitting phosphor according to the present application is obtained by firing a powder obtained by mixing these materials at a high temperature in the air atmosphere. The ultraviolet light-emitting phosphor can be obtained by performing this high temperature firing in the air atmosphere at 1000° C. to 1350° C. for 30 minutes to 10 hours.

The uses of the ultraviolet light-emitting phosphor thus obtained are various. For example, clean disinfection by ultraviolet rays with residues and environmental damage suppressed can be performed by disinfecting various organisms to be disinfected using ultraviolet light emitted by the ultraviolet light-emitting phosphor according to the present application. The decomposition treatment of hardly decomposed substances (such as formaldehyde and PCB) and the synthesis of new chemical substances (for example, photocatalyst substance or the like) can also be performed by using this ultraviolet light. The ultraviolet light-emitting phosphor can also be applied to various medical fields such as the medical treatment of intractable diseases (such as atopic dermatitis) and the prevention of hospital infection by using this ultraviolet light.

The ultraviolet light-emitting phosphor can be used as various light-emitting elements comprising such an ultraviolet light-emitting phosphor. The phosphor can also be used for light-emitting devices, comprising the light-emitting element.

EXAMPLES

In order to clarify the characteristics of the present invention further, Examples are shown below, but the present invention is not limited by these Examples.

Example 1

(1-1) Manufacturing of Phosphors

Aluminum oxide ($Al_2O_3$), yttrium oxide ($Y_2O_3$) and scandium oxide ($Sc_2O_3$) were used as raw materials and mixed at stoichiometric proportions that were identical to the compositions of desired phosphors, respectively. The mixed powders were fired in the air atmosphere at 1300° C. for 5 hours.

(1-2) Identification of Phosphors

Figure 2:
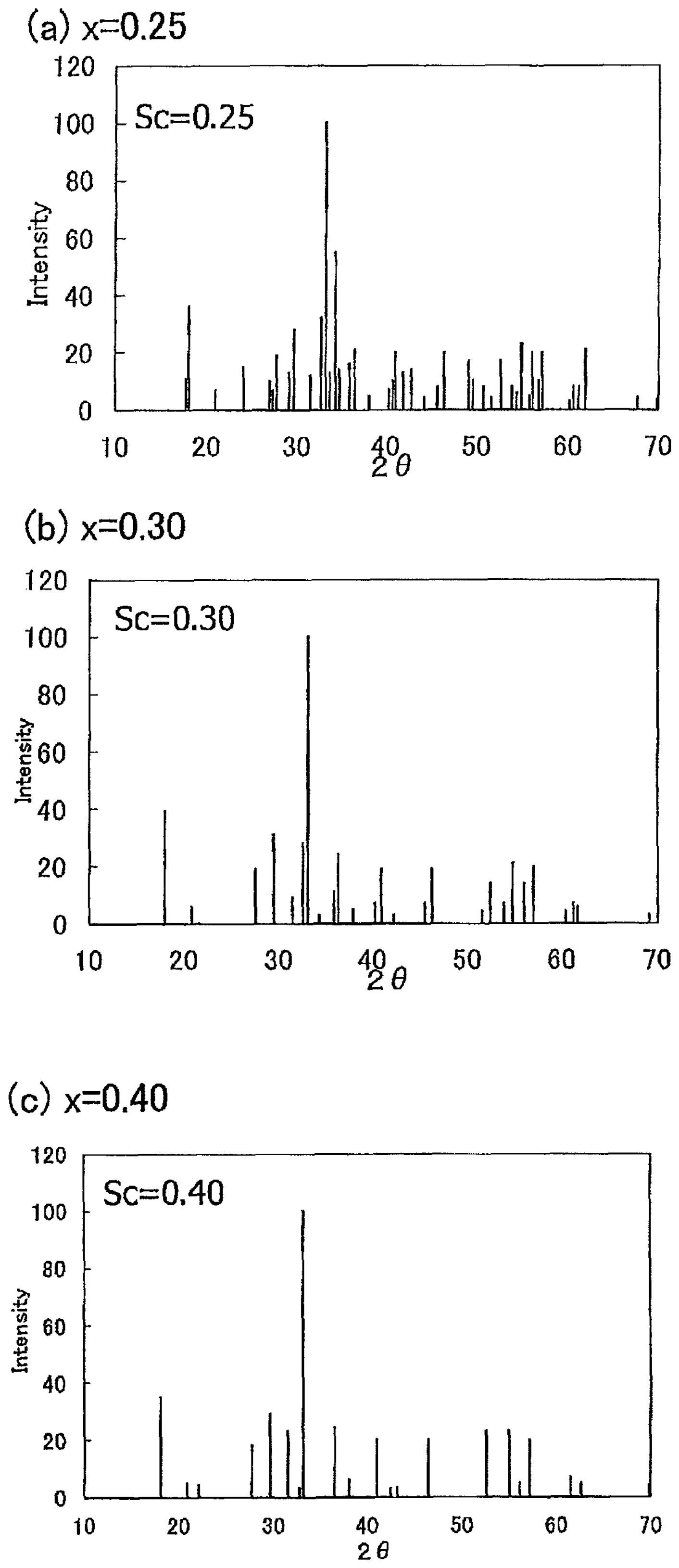
FIG. 2 shows the X-ray diffraction results of the ultraviolet light-emitting phosphors according to Example 1 of the present invention.
Figure 3:
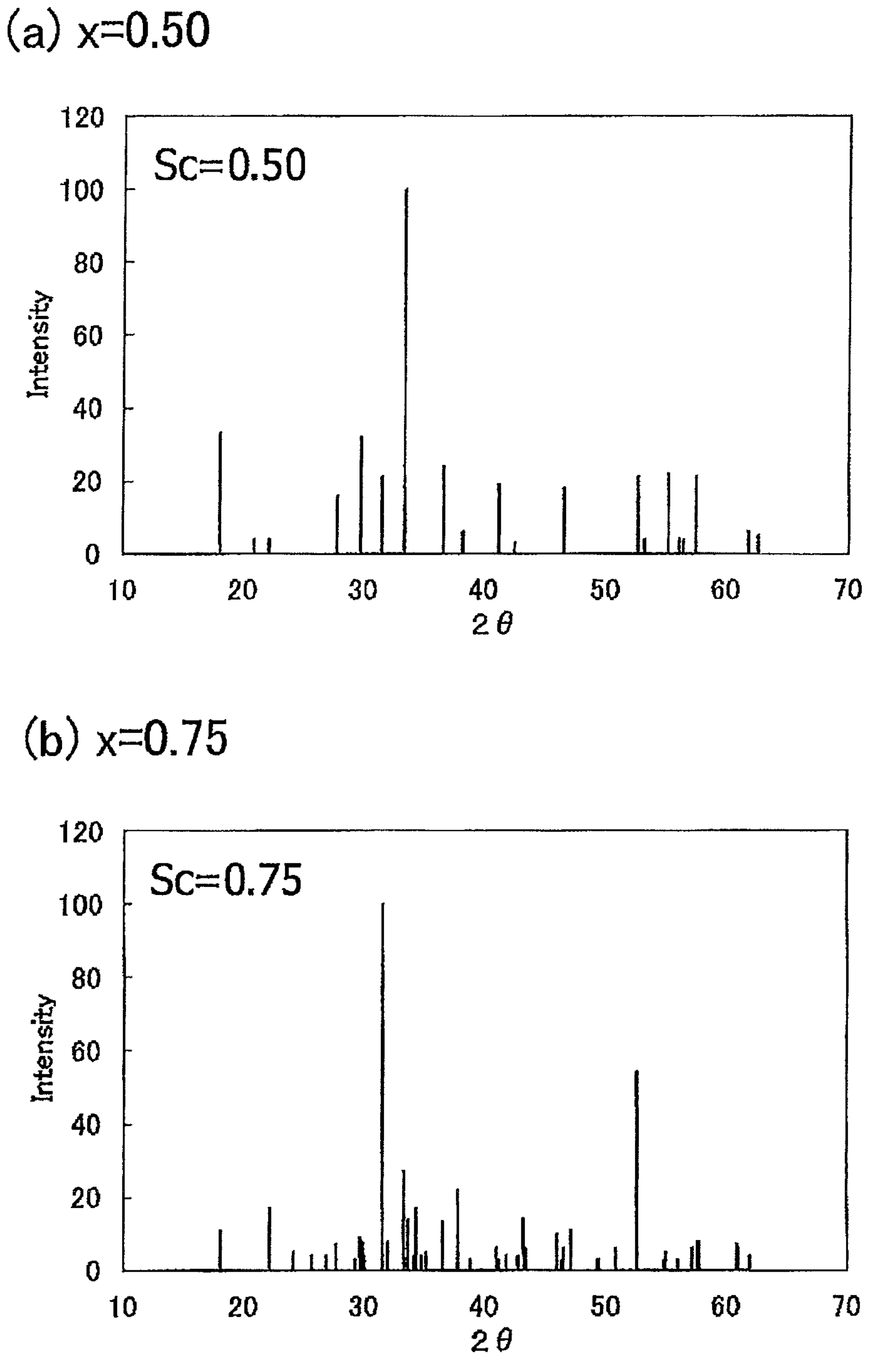
FIG. 3 shows the X-ray diffraction results of the ultraviolet light-emitting phosphors according to Example 1 of the present invention.

X-ray diffraction results acquired by an X-ray diffraction device a radiation source of which is FeKα regarding sintered bodies (the fractional content of Sc x: 0.007, 0.02, 0.10, 0.25, 0.30, 0.40, 0.50, 0.75) obtained above are shown in FIG. 1 to FIG. 3. From the peak values acquired in FIG. 1 to FIG. 3, it was confirmed that $(Y_{1-x}Sc_x)AlO_3$ (wherein $0 \leq x \leq 1$) is surely crystallized in all the sintered bodies. It was confirmed from these X-ray diffraction results especially that the crystal structures of main products in the case where the fractional content of Sc was 0.02 or less were a $YAlO_3$ phase (space group Pnma). Peaks having 2θ at 20° or less were detected as to the crystal structures of products in the case where the fractional content of Sc was 0.1 or more. It was confirmed that these were a $YAlO_3$ phase (space groups P63/mmc). It was confirmed that these two types of $YAlO_3$ phases (space group Pnma and P63/mmc) were intermingled as to the crystal structures of products in the case where the fractional content of Sc was 0.10 or more.

(1-3) Measurement of Emission Intensity

Figure 4:
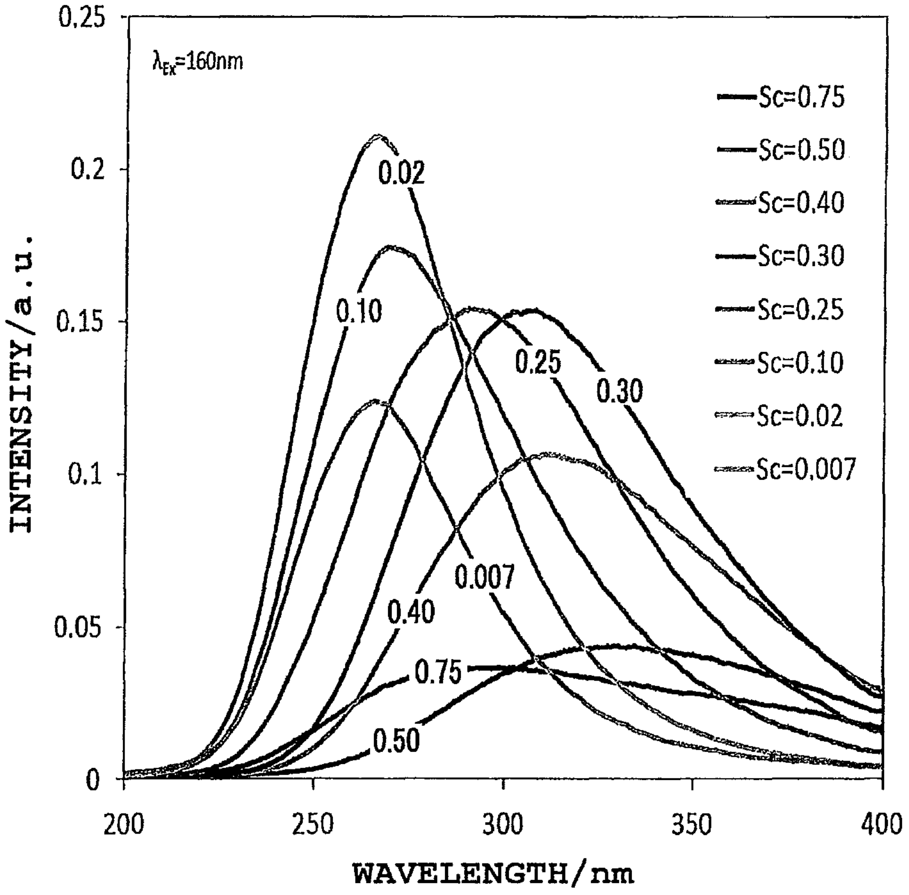
FIG. 4 shows the results of emission intensity spectra as to ultraviolet light emission by the ultraviolet light-emitting phosphors according to Example 1 of the present invention.

The phosphors obtained above were irradiated with vacuum ultraviolet rays emitted using a deuterium lamp L1835 (manufactured by Hamamatsu Photonics K.K.) having an excitation wavelength of 146 nm as a light source. Results of emission intensity spectra as to emitted light obtained by this irradiation is shown in FIG. 4. In the graph of the emission intensity spectra of FIG. 4, the wavelength (nm) is shown on the horizontal axis, and the emission intensity (integrated emission intensity) (a.u.) is shown on the vertical axis. A graph on which the integrated emission intensities based on the results of these emission intensity spectra are plotted versus the fractional content of yttrium (Y) (1-x) is shown in FIG. 5.

It was confirmed from the results of FIG. 4 that light in the ultraviolet region emitted from all the ultraviolet light-emitting phosphors $(Y_{1-x}Sc_x)AlO_3$ according to this Example was obtained by vacuum ultraviolet ray excitation. Among these, especially in the phosphors such that $0.007 \leq x \leq 0.50$, the wavelengths of stronger peaks were confirmed. Additionally, among these, in the phosphors such that $0.007 \leq x \leq 0.40$, the wavelengths of still sharper peaks were confirmed.

Figure 5:
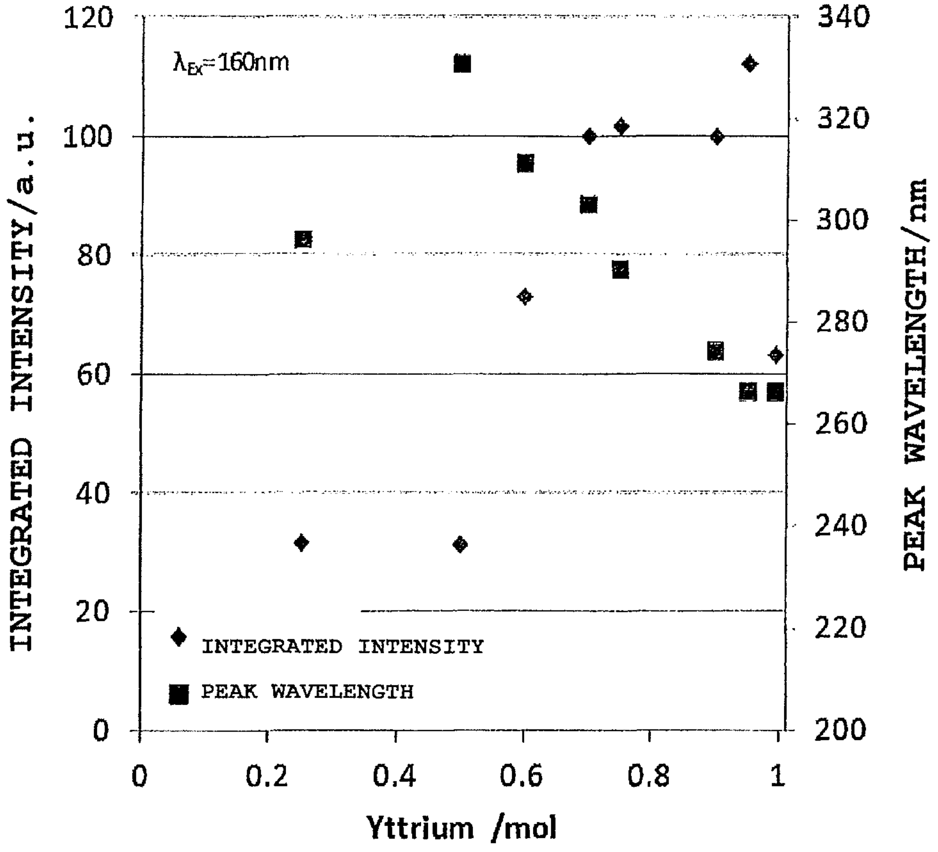
FIG. 5 shows a graph on which integrated emission intensities as to ultraviolet light emission by the ultraviolet light-emitting phosphors according to Example 1 of the present invention are plotted versus the fractional contents of yttrium element (Y) (1-x).

It was also confirmed from the results of FIG. 5 that light in the ultraviolet region emitted from all the ultraviolet light-emitting phosphors $(Y_{1-x}Sc_x)AlO_3$ according to this Example was obtained by vacuum ultraviolet ray excitation. It was confirmed that the integrated emission intensity (a.u.) as to ultraviolet light emission is improved dramatically especially when the fractional content of yttrium element (Y) (1-x) exceeded 0.60 (namely, x became smaller than 0.40). It was also confirmed at the same time that the peak wavelength was shortened gradually from around 300 nm.

To summarize, the ultraviolet light-emitting phosphors $(Y_{1-x}Sc_x)AlO_3$ in this Example, not particularly limited to, but with $0.007 \leq x \leq 0.50$ was observed to have the wavelengths of stronger peaks. Further, it was confirmed that the ultraviolet light-emitting phosphors with $0.007 \leq x \leq 0.40$ exhibited the excellent characteristics that strong ultraviolet light having peak wavelengths at shorter wavelengths than around 300 nm was emitted and the integrated emission intensities thereof were also improved dramatically at the same time.

Example 2

(2-1) Evaluation of Deterioration Resistance

The evaluation of degradation resistance (evaluation of durability) was performed on the ultraviolet light-emitting phosphors $(Y_{1-x}Sc_x)AlO_3$ obtained in the above-mentioned Example 1. The evaluation of durability was also performed on phosphors $ZnAl_2O_4$ and $YAlO_3$:Pr, which were known conventionally, as a Comparative Examples. (Samples: Comparative Example ($ZnAl_2O_4$), Comparative Example ($YAlO_3$:Pr), the present Example $(Y_{1-x}Sc_x)(AlO_3)$)

The mixing ratio of a phosphor to a solvent was set at 1:1. The phosphor and the solvent were mixed in a glass bottle by stirring for 5 minutes. The obtained mixed solution was poured into an alumina dish and spread. The obtained mixed solution was fired in the air atmosphere at 700° C. for 30 minutes, and the obtained powder was then collected by a medicine spoon. The collected powder was filled in a holder for measurement. Emission spectra were measured and evaluated at an excitation wavelength of 146 nm using a deuterium lamp L1835 (manufactured by Hamamatsu Photonics K.K.) for a light source and using a vacuum ultraviolet spectroscopic system for excitation (manufactured by JASCO Corporation) as a measuring device.

Figure 6:
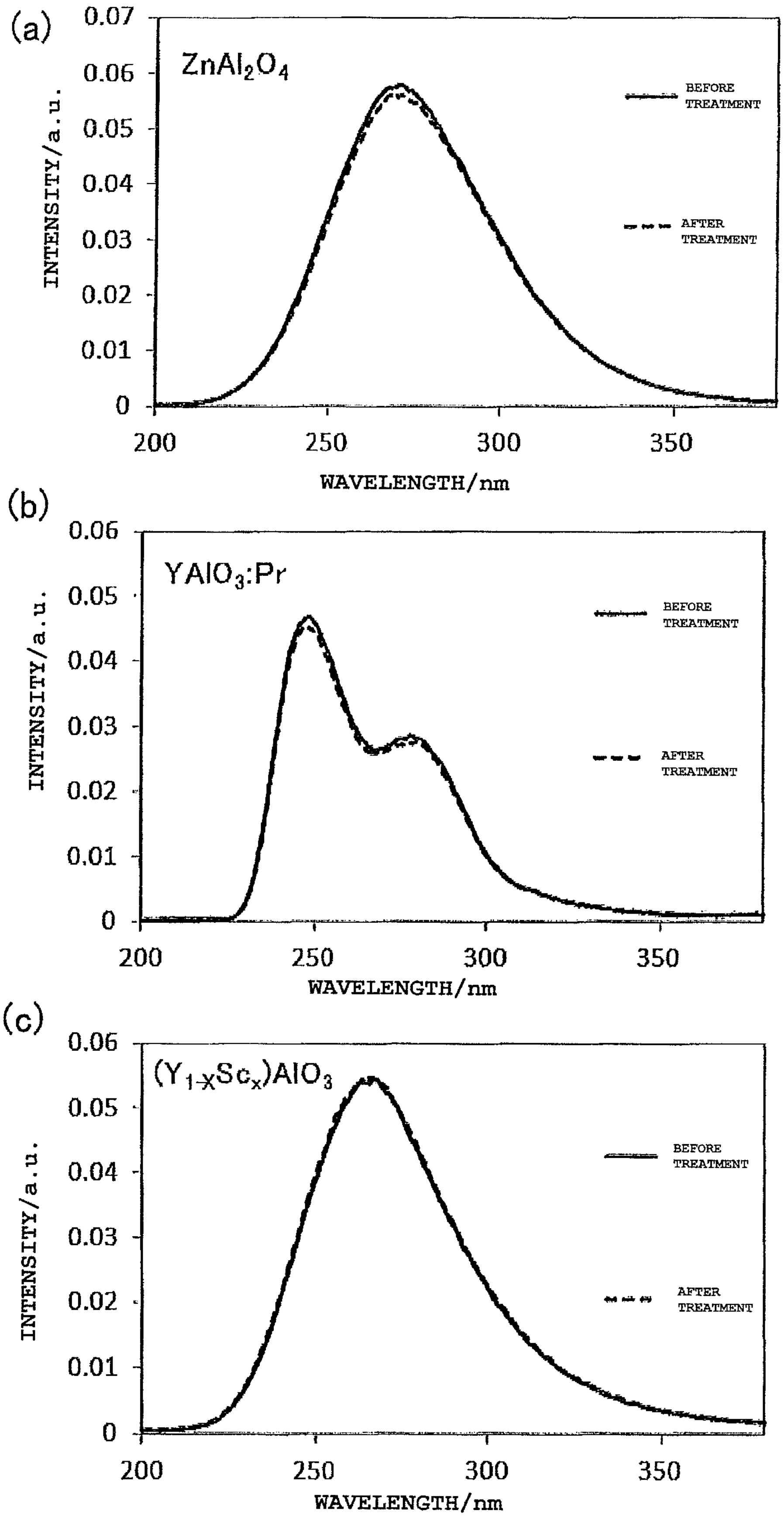
FIG. 6 shows the results of the emission intensity spectra as to the evaluation of the degradation resistance of an ultraviolet light-emitting phosphor according to Example 2 of the present invention and Comparative Examples (phosphors $ZnAl_2O_4$ and $YAlO_3$:Pr).

The obtained emission spectra are shown in FIG. 6, and the changes in intensity in the case where integrated intensities are calculated from these emission spectra are shown in the following Table at the same time.

TABLE 1

| Sample | Change in intensity |
|---|---|
| $ZnAl_2O_4$ | 97.1 |
| $YAlO_3$:Pr | 97.7 |
| The present Example | 100.8 |

As is apparent from the obtained results, the intensities of Comparative Examples $ZnAl_2O_4$ and $YAlO_3$:Pr were found to decrease, but the intensity of the present Example $(Y_{1-x}Sc_x)AlO_3$ was not found to decrease, and it was confirmed that the intensity of the present Example $(Y_{1-x}Sc_x)AlO_3$ was rather heighten. The ease of being subject to the influence of heat and an organic solvent can be considered as a cause of this difference. Specifically, it was shown that the present Example $(Y_{1-x}Sc_x)AlO_3$ was by far more stable also as to heat and an organic solvent than the phosphors of Comparative Examples. From another viewpoint, in the phosphor $(Y_{1-x}Sc_x)AlO_3$ according to the present Example, it is presumed that Sc forms a state difficult to change in valence, and it is therefore considered that the degradation resistance is enhanced as to various external factors.

The invention claimed is:

1. An ultraviolet light-emitting phosphor consisting of a yttrium element, a scandium element, an aluminum element and an oxygen element, wherein the ultraviolet light-emitting phosphor is excited by irradiation of vacuum ultraviolet rays or electron beams to emit ultraviolet rays, wherein the ultraviolet light-emitting phosphor is represented by a general formula $(Y_{1-x}Sc_x)AlO_3$ (wherein $0<x<1$).

2. The ultraviolet light-emitting phosphor according to claim 1, wherein $0.007 \leq x \leq 0.50$.

3. A light-emitting element, comprising the ultraviolet light-emitting phosphor according to claim 1.

4. A light-emitting device, comprising the light-emitting element according to claim 3.

5. A light-emitting element, comprising the ultraviolet light-emitting phosphor according to claim 2.

6. A light-emitting device, comprising the light-emitting element according to claim 5.

* * * * *